United States Patent
Weickgenannt et al.

(10) Patent No.: US 10,927,066 B2
(45) Date of Patent: Feb. 23, 2021

(54) PROCESS FOR HYDROGENATING A MIXTURE IN THE PRESENCE OF A COLORLESS AMINE

(71) Applicant: BASF SE, Ludwigshafen am Rhein (DE)

(72) Inventors: Andreas Weickgenannt, Ludwigshafen (DE); Silvia Tauro, Ludwigshafen (DE); Alexander Duefert, Ludwigshafen (DE); Viktor Ladnak, Ludwigshafen (DE); Kai Thiele, Antwerp (BE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 16/333,142

(22) PCT Filed: Aug. 31, 2017

(86) PCT No.: PCT/EP2017/071855
§ 371 (c)(1),
(2) Date: Mar. 13, 2019

(87) PCT Pub. No.: WO2018/050441
PCT Pub. Date: Mar. 22, 2018

(65) Prior Publication Data
US 2019/0210955 A1    Jul. 11, 2019

(30) Foreign Application Priority Data
Sep. 14, 2016  (EP) .................................... 16188851

(51) Int. Cl.
| C07C 209/72 | (2006.01) |
| C07C 209/84 | (2006.01) |
| C07C 209/90 | (2006.01) |
| C07C 209/82 | (2006.01) |
| C07C 263/10 | (2006.01) |

(52) U.S. Cl.
CPC .......... *C07C 209/72* (2013.01); *C07C 209/82* (2013.01); *C07C 209/84* (2013.01); *C07C 209/90* (2013.01); *C07C 263/10* (2013.01)

(58) Field of Classification Search
CPC ... C07C 209/72; C07C 209/82; C07C 209/84; C07C 209/90; C07C 263/10
See application file for complete search history.

(56) References Cited

U.S. PATENT DOCUMENTS

| 2,019,032 A | 10/1935 | Weiss et al. |
| 3,222,310 A | 12/1965 | Hinckley et al. |
| 5,889,070 A * | 3/1999 | Schilling ............ C08G 18/3237 521/155 |
| 6,140,382 A * | 10/2000 | Gallus ................... C07C 263/10 521/155 |
| 8,853,443 B2 | 10/2014 | Breuninger et al. |
| 2004/0000471 A1* | 1/2004 | Su .......................... C07C 213/10 203/2 |
| 2004/0026226 A1* | 2/2004 | Heuer .................. C07C 209/90 203/59 |
| 2005/0014975 A1* | 1/2005 | Strofer .................. C07C 209/78 564/330 |
| 2009/0149671 A1* | 6/2009 | Stutz ..................... C07C 263/10 560/347 |
| 2009/0240077 A1 | 9/2009 | Wershofen et al. |
| 2012/0046497 A1* | 2/2012 | Stroefer ................ C07C 209/78 564/333 |
| 2012/0108843 A1* | 5/2012 | Schelling .............. C07C 263/10 560/341 |
| 2013/0204044 A1* | 8/2013 | Mehta ................... C07C 209/84 564/498 |
| 2017/0260115 A1 | 9/2017 | Weidert et al. |
| 2018/0002303 A1 | 1/2018 | Duefert et al. |
| 2018/0044179 A1 | 2/2018 | Schelling et al. |
| 2018/0222830 A1 | 8/2018 | Duefert et al. |
| 2018/0327347 A1 | 11/2018 | Weickgenannt et al. |
| 2020/0148629 A1* | 5/2020 | Knauf .................. B01J 19/0013 |

FOREIGN PATENT DOCUMENTS

| CA | 2209139 A1 | 12/1997 |
| EP | 0 816 333 A1 | 1/1998 |
| WO | WO 2010/057909 A1 | 5/2010 |
| WO | WO 2016/083175 A1 | 6/2016 |
| WO | WO 2016/110520 A1 | 7/2016 |
| WO | WO 20171125302 A1 | 7/2017 |

OTHER PUBLICATIONS

International Search Report dated Nov. 6, 2017 in PCT/EP2017/071855, 2 pages.
International Preliminary Report on Patentability dated Sep. 27, 2018 in PCT/EP2017/071855 filed Aug. 31, 2017 (with English translation), 9 pages.
Ulrich, H. "Chemistry and Technology of Isocyanates" John Wiley & Sons, 1996, 6 pages.

* cited by examiner

*Primary Examiner* — Alexander R Pagano
(74) *Attorney, Agent, or Firm* — Oblon, McClelland, Maier & Neustadt, L.L.P.

(57) ABSTRACT

The present invention relates to a process for hydrogenating a mixture (G1) in the presence of a catalyst, where the mixture (G1) comprises at least one colorless amine and at least one color-imparting component. As a result of the hydrogenation step, the at least one color-imparting component is firstly partially, preferably fully, hydrogenated, while the colorless amine, in particular aniline, is not hydrogenated or hydrogenated to only a very small extent. The color-imparting components which cause the discoloration of the amine which is itself in principle colorless are thus removed by hydrogenation, as a result of which purification of the colorless amine or the mixture (G1) is achieved.

16 Claims, No Drawings

PROCESS FOR HYDROGENATING A MIXTURE IN THE PRESENCE OF A COLORLESS AMINE

This application is a National Phase of PCT/EP2017/071855, which was filed on Aug. 31, 2017. This application is based upon and claims the benefit of priority to European Application No. 16188851.6, which was filed on Sep. 14, 2016.

The present invention relates to a process for hydrogenating a mixture (G1) in the presence of a catalyst, where the mixture (G1) comprises at least one colorless amine and at least one color-imparting component. As a result of the hydrogenation step, the at least one color-imparting component is firstly partially, preferably fully, hydrogenated, while the colorless amine, in particular aniline, is not hydrogenated or hydrogenated to only a very small extent. The color-imparting components which cause the discoloration of the amine which is itself in principle colorless are thus removed by hydrogenation, as a result of which purification of the colorless amine or the mixture (G1) is achieved.

Processes for purifying amines and for removing color-imparting components, e.g. in aniline, are described in the prior art.

U.S. Pat. No. 3,222,310 discloses a method of inhibiting color formation in amines. Here, colorless aniline is admixed with alkali metal borohydrides and is also color-stable after contact with atmospheric oxygen. In this disclosure, the aniline used is already colorless, and removal of color-imparting components is not described, nor is the use of catalysts.

U.S. Pat. No. 2,019,032 discloses a process for aromatic amines, with aniline being mentioned by way of example, which display only a barely perceptible color change on contact with atmospheric oxygen as a result of the addition of small amounts of maleic anhydride before a final distillation.

US 2009/0240077 A1 describes a process for preparing diamines and polyamines of the diphenylmethane series by reaction of aniline and formaldehyde in the presence of an acid catalyst, in which the aniline used comprises a total of less than 0.5% by weight, based on the weight of the aniline used, of compounds which comprise at least one carbonyl group or are formed by reaction of these compounds comprising at least one carbonyl group with aniline.

WO 2010/057909 discloses a process for preparing an isocyanate, which comprises hydrogenation of an amine-comprising mixture (Gi) in the presence of a copper-comprising hydrogenation catalyst to give a mixture (Gii) comprising the amine and reaction of the mixture (Gii) with phosgene to give a mixture (Gii) comprising the isocyanate. The amine comprised in the mixture (Gi) is preferably a diamine or polyamine of the diphenylmethane series, e.g. MDI, which is obtained, for example, by reaction of aniline with formaldehyde. Furthermore, WO 2010/057909 relates to the isocyanate which can be prepared by this process. It is not disclosed that the mixture (G1) can itself comprise a color-imparting substance. The mixture (Gi) typically comprises at least one precursor of a color-imparting substance, i.e. a color-imparting substance results therefrom only in the phosgenation stage. Examples mentioned are N-formylated diamines and/or N-formylated polyamines of the diphenylmethane series or compounds of the 3,4-dihydroquinazoline class. No mention is made of any impurities from the preparation of the precursor of the mixture (Gi), i.e. impurities which can be formed in the preparation of, for example, colorless monoamines such as aniline.

The processes described in the prior art show that there is a need for amines which are colorless or virtually colorless, particularly in order for them to be available as very pure starting material for further industrial use. The processes described in the prior art have, for example, the disadvantage that the color formation in an amine such as aniline is merely inhibited or that it is not a colorless amine such as aniline but instead downstream products thereof which are purified in the later course of syntheses in which an amine such as aniline is used. Accordingly, there is a need for a process for purifying amines which makes colorless or virtually colorless amines available.

It is therefore an object of the present invention to provide a process for purifying amines, by means of which an amine-comprising mixture which is colorless or virtually colorless can be obtained.

The object is achieved by a process for hydrogenating a mixture (G1) which comprises at least one colorless amine and at least one color-imparting component, where the at least one color-imparting component is selected from among cycloaliphatic carbonyl compounds, cycloaliphatic amines, cycloaliphatic imines and C6-ring aromatics, wherein the mixture (G1) is hydrogenated in the presence of a catalyst to give a mixture (G2) in which the at least one color-imparting component is at least partially or completely hydrogenated.

A great advantage of the process of the invention is that the process of the invention makes purification of the mixture (G1) possible. This is, in particular, important in the further processing of the mixture (G2) obtained by means of the hydrogenation, since the purer the components of the mixture (G2) are, the purer are the later products obtained by reaction of the mixture (G2). In addition, this contributes considerably to lowering the costs of relatively long syntheses. It is therefore particularly valuable to carry out the purification of starting materials which are right at the beginning of relatively long syntheses (e.g. aniline).

A further advantage of the process of the invention is that a time-consuming and costly work-up after the hydrogenation can be avoided.

An additional advantage of the process of the invention is that the proportion of the amine in the mixture does not become smaller, or becomes only insignificantly smaller, during the purification.

It is therefore particularly advantageous, according to the invention, for catalysts comprising copper and/or palladium to be used in hydrogenation of the mixture (G1), as a result of which the color values of the amine are improved and a colorless or virtually colorless mixture (G2) comprising the corresponding amine is thus made available. Furthermore, it is advantageous that the proportion of the colorless amine in the mixture is not reduced, or is reduced only insignificantly, during the hydrogenation.

A further advantage of the process of the invention is, when the purified amine is, for example, aniline, that this can be used, for example, for synthesizing the compounds methylenedianiline (MDA) and methylenedi(phenyl isocyanate) (MDI) which then likewise have an advantageous color, which is especially important for further industrial use.

A further advantage of the process of the invention is that, as a result of the purification of a component such as an amine which is so fundamental to many processes, further purification steps in subsequent processes can be saved and these processes thus become more economical.

In addition, it is also advantageous that the mixture (G2) obtained by means of the hydrogenation has a high long-term color stability.

For the purposes of the present invention, the term "purification" refers to a process in which the purity of the amine present in mixture (G1) is improved, in particular by hydrogenation of color-imparting components comprised in the mixture.

The terms "colorless" and "colorless amine" as are used for the purposes of the present patent application refer to the color number L*, measured in accordance with DIN 5033 (2009), of at least one compound, which is at least 90, preferably at least 95, particularly preferably at least 98.

The terms "color-imparting" and "color-imparting component" as are used for the purposes of the present patent application refer to the color number L*, measured in accordance with DIN 5033 (2009), of at least one compound, which is less than 90, preferably not more than 80, more preferably not more than 75.

The process of the invention for hydrogenating amines is defined in more detail below.

A mixture (G1) comprising at least one colorless amine and at least one color-imparting component is hydrogenated in the presence of a catalyst.

The mixture (G1) comprises at least one colorless amine. Colorless amines per se are known to those skilled in the art from the prior art.

The at least one colorless amine can be a primary amine, an aromatic amine and/or a monoamine, preferably a primary aromatic amine, a primary monoamine and/or an aromatic monoamine, particularly preferably a primary aromatic monoamine, very particularly preferably aniline. In particular, the colorless amine is aniline.

The at least one colorless amine comprised in the mixture (G1) is preferably present in an amount of at least 80% by weight, particularly preferably at least 90% by weight, very particularly preferably at least 95% by weight, based on the total weight of the mixture (G1).

The term "total weight of the mixture (G1)" as used for the purposes of the present patent application refers to the sum of the weights of the at least one colorless amine and the at least one color-imparting component in the mixture (G1). Additional constituents (components) which are possibly also present, e.g. solvents, are not included here but are additionally indicated, optionally in relation to the total weight of the mixture (G1).

Color-imparting components in the context of the present invention are known to those skilled in the art from the prior art. These occur, for example, in the mixture (G1) as a result of the process or are, for example, formed by contact of the mixture (G1) or the components comprised therein with oxidizing media, for example atmospheric oxygen.

The at least one color-imparting component is selected from among cycloaliphatic carbonyl compounds, cycloaliphatic amines, cycloaliphatic imines and C6-ring aromatics.

For the purposes of the present invention, cycloaliphatic carbonyl compounds, cycloaliphatic amines and cycloaliphatic imines include both the corresponding saturated compounds and the corresponding unsaturated compounds. These compounds can optionally be substituted, for example, by one or more alkyl or hydroxy radicals.

The term "C6-ring aromatic" refers, for the purposes of the present patent application, both to unsubstituted benzene and to substituted benzene.

When the C6-ring aromatic is a substituted benzene, this can be substituted in one or more positions. The substituents are, independently of one another, preferably alkyl, hydroxy, halogen, amino and/or nitro radicals.

The at least one color-imparting component in the mixture (G1) is preferably selected from among cyclohexylphenylamine derivatives, cyclohexanone derivatives, cyclohexenone derivatives, cyclohexylamine derivatives, N-methylcyclohexylamine derivatives, toluidine derivatives, nitrobenzene derivatives, 2-aminophenol derivatives, 1,2-phenylenediamine derivatives, diphenylamine derivatives, oxidized N-methylaniline derivatives and unoxidized N-methylaniline derivatives, particularly preferably from among cyclohexylphenylamine derivatives, cyclohexylamine derivatives, N-methylcyclohexylamine derivatives, oxidized N-methylaniline derivatives and unoxidized N-methylaniline derivatives.

The term "derivative" here encompasses both the respective parent compounds and also the compounds derived therefrom, in which, for example, one or more H atoms are replaced by other functional groups. If the derivative is, for example, a cyclohexanone derivative, the term "derivative" encompasses both the pure cyclohexanone (parent compound) and also the compounds derived therefrom, for example 3-methylcyclohexanone.

The at least one color-imparting component comprised in the mixture (G1) is preferably present in an amount of not more than 5% by weight, particularly preferably not more than 2% by weight, very particularly preferably not more than 1% by weight, based on the total weight of the mixture (G1).

In one embodiment of the present invention, the mixture (G1) is recycled aniline, where the recycled aniline comprises at least one color-imparting component selected from among cycloaliphatic carbonyl compounds, cycloaliphatic amines, cycloaliphatic imines and C6-ring aromatics.

Furthermore, the mixture (G1) can comprise further constituents such as solvents in addition to the at least one colorless amine and the at least one color-imparting component. If such constituents (components) are comprised in the mixture (G1), the corresponding amounts of these constituents are additionally indicated in relation to the total weight of the mixture (G1). Preference is given to no further constituents being present in the mixture (G1) or such constituents being present in an amount of not more than 10%, based on the total weight of the mixture (G1), i.e. the sum of colorless amines and color-imparting components.

The mixture (G1) is hydrogenated in the presence of a catalyst to give a mixture (G2) in which the at least one color-imparting component is at least partially or completely hydrogenated.

The expression "at least partially hydrogenated" as is used for the purposes of the present patent application means that the at least one color-imparting component has been hydrogenated to a percentage extent of at least 50% by weight, preferably at least 60% by weight, more preferably at least 70% by weight, based on the total weight of the at least one color-imparting component in mixture (G1).

The mixture (G2) after the hydrogenation comprises a major part of the colorless amine (from the mixture (G1)), for example at least 90% by weight, preferably at least 94% by weight, more preferably at least 96% by weight, particularly preferably at least 99% by weight, of the at least one colorless amine, based on the total amount of the colorless amine comprised in the mixture (G1).

The color of a mixture can be determined by various methods, for example with the aid of the CIE color scale. This is defined by the values L*, a* and b*. L* is a measure of the lightness of the sample (0-100, 100 is the lightest, i.e.

colorless), a* denotes the green component (negative values) or red component (positive values), b* denotes the blue component (negative values) or yellow component (positive values). In the case of a* and b*, a value of 0 denotes a colorless sample.

For the purposes of the present invention, the term "lightness" is equivalent to the term "colorlessness".

In the process of the invention, the values of the color numbers L* and b* are particularly important.

The mixtures (G1) according to the invention preferably have a color number L*, measured in accordance with DIN 5033 (2009), of at least 50.

The at least one colorless amine comprised in mixture (G1) preferably has a color number L*, measured in accordance with DIN 5033 (2009), of at least 90, preferably at least 95, particularly preferably at least 98.

The mixtures (G2) according to the invention preferably have a color number L*, measured in accordance with DIN 5033 (2009), of at least 90, particularly preferably at least 95, very particularly preferably at least 98.

The mixtures (G2) according to the invention preferably have a color number b*, measured in accordance with DIN 5033 (2009), of not more than 20, particularly preferably not more than 15, very particularly preferably not more than 10.

In the process of the present invention, the mixture (G1) is hydrogenated in the presence of a catalyst.

Possible catalysts are in principle all suitable hydrogenation catalysts known to those skilled in the art. In connection with the present invention, preference is given to using catalysts which do not hydrogenate, or only slightly hydrogenate, primary amines.

In the process of the invention, preference is given to using catalysts which comprise copper, palladium, cobalt, rhenium and/or manganese, particularly preferably copper and/or palladium. The abovementioned elements such as copper thus form the catalytically active component of the corresponding catalyst, which can also comprise further components such as support materials.

The catalyst which is used in the process of the invention can comprise copper in an amount in the range from 0.1 to 100% by weight, preferably in the range from 20 to 80% by weight, based on the total weight of the catalyst and calculated as metal, and/or palladium in an amount in the range from 0.1 to 100% by weight, preferably in the range from 0.1 to 30% by weight, based on the total weight of the catalyst and calculated as metal.

Here, the expression "calculated as metal" indicates that the amount reported relates to the elemental metal.

If the catalyst comprises copper, the copper can be present as metal or as copper compound or as a mixture of at least two copper compounds or as a mixture of metal and a copper compound or as a mixture of metal and at least two copper compounds in the catalyst.

Possible copper compounds are preferably copper chromate, copper chromite, copper oxide, copper nitrate, copper sulfate, copper chloride, copper bromide, copper iodide, copper carbonate, copper acetylacetate, copper alkoxide, copper aryloxide or copper carboxylate, particularly preferably copper chromite or copper oxide.

If the catalyst comprises palladium, the palladium can be present as metal or as palladium compound or as a mixture of at least two palladium compounds or as a mixture of metal and a palladium compound or as a mixture of metal and at least two palladium compounds in the catalyst.

The catalysts used in the process of the invention can be present in either supported or unsupported form. The support material is a support material which is inert or substantially inert under the reaction conditions and is preferably selected from the group consisting of carbon, silicon oxide, aluminum oxide, manganese oxide, cerium oxide, zirconium oxide, lanthanum oxide, titanium oxide and mixtures of two or more of these materials. The catalyst is preferably present in supported form or as unsupported metal catalyst. The catalyst can be used either as powder or as shaped bodies, preferably as shaped bodies.

In the process of the invention, hydrogen gas ($H_2$), particularly preferably technical-grade hydrogen, is preferably used as hydrogenating agent.

For the purposes of the present invention, "technical-grade" means a hydrogen content of preferably at least 99% by weight, particularly preferably at least 99.5% by weight, based on the total weight of the hydrogen.

Furthermore, the hydrogenating agent can also be a mixture of hydrogen and inert gas, with the inert gas being able to be helium, argon, carbon dioxide, nitrogen or neon. Formic acid or other comparable hydrogen-liberating compounds can likewise be used.

The hydrogenating process can be carried out continuously or discontinuously (batch process); the process of the invention is preferably carried out continuously.

In the case of discontinuous operation, the hydrogenation can, for example, be realized in a stirred vessel or a stirring autoclave, a loop reactor, a jet loop reactor, a bubble column or a fixed-bed reactor having a pumped circuit; the hydrogenation is preferably realized in a stirred vessel or a stirring autoclave. In the case of discontinuous operation, the mixture (G1) and the catalyst are preferably all placed in the reactor at the beginning. Here, the catalyst can be introduced as fixed bed or in another form. In the process of the invention, the preferred embodiment is a suspension of catalyst in the mixture (G1).

In the case of continuous operation, the hydrogenation is, for example, carried out in a continuously operated stirred tank reactor, a continuously operated loop reactor, a continuously operated jet loop reactor, a continuously operated bubble column, a continuously operated fixed-bed reactor having a pumped circuit or a cascade of stirred vessels. In the case of continuous operation, the mixture (G1) is introduced continuously and the product mixture (G2) obtained, which comprises the purified amine, is discharged. In the case of the continuous mode of operation, the catalyst is preferably present as fixed bed in the reactor and is replaced and/or regenerated only when required.

The hydrogenation of the mixture (G1) can be carried out at temperatures known from the prior art. The hydrogenation of the mixture (G1) is preferably carried out at a temperature in the range from 90° C. to 300° C., particularly preferably from 90° C. to 200° C., very particularly preferably from 90° C. to 150° C.

The hydrogenation time is preferably in the range from 1 to 100 hours, particularly preferably from 5 to 80 hours, very particularly preferably from 10 to 50 hours. The hydrogenation is preferably carried out until the mixture (G2) having the desired quality is attained.

In this context, the term "desired quality" means that the mixture (G2) after the hydrogenation step has a better color or a higher L* value and/or a very low b* value (0 is the optimum) than the mixture (G1).

The product mixture (G2) obtained can be worked up in a conventional way, as is known for those skilled in the art.

For example, the product mixture (G2) obtained can be worked up further by means of a solid-liquid separation or by distillation, preferably by distillation, in order to isolate the at least one colorless amine, separate off the catalyst and/or remove the hydrogenation products from the mixture (G2).

The separation of the catalyst from the product mixture (G2) can in the case of a discontinuous process be carried out by, for example, a solid-liquid separation such as filtration, sedimentation or centrifugation.

The distillation of the mixture (G2) is preferably carried out with the aid of evaporators and/or columns. The columns known to those skilled in the art are suitable for this purpose. Preference is given to packed columns, tray columns having sieve trays, columns having dual-flow trays, columns having bubble cap trays or rectification columns equipped with valve trays, dividing wall columns or thin-film evaporators and falling-film evaporators. The column used preferably has a number of theoretical plates ($N_{th}$) of from 1 to 100, particularly preferably from 1 to 50. The distillation is preferably carried out in the absence of oxygen.

For the purposes of the present invention, the term "absence of oxygen" means that the proportion by volume of oxygen is less than 1%, preferably less than 0.01%, particularly preferably less than 0.01% and very particularly preferably less than 0.001%, based on the total volume of the distillation column.

The distillation is preferably carried out at a pressure at the top of from 1 to 100 mbar. The process can be carried out discontinuously or continuously.

When the distillation is carried out discontinuously, the mixture (G2) is initially placed in a reactor, preferably with exclusion or air, and heated. After the steady state has been attained, fractions can be taken off.

In the case of continuous distillation, the column is adjusted so that a reflux ratio of from 1 to infinity, preferably from 1 to 10, results.

For the purposes of the present invention, the reflux ratio is defined as the mass ratio of condensate returned to the column and condensate taken off as distillate at the top of a distillation column.

Continuous operation of the process is carried out with the aid of a column which is preferably equipped with a vaporizer and an overhead condenser.

In at least one further process step, the colorless amine comprised in the mixture (G2) can be converted into a diphenylmethane derivative and the diphenylmethane derivative can optionally be converted into an aromatic isocyanate in at least one further step. Preference is given to the colorless amine firstly being converted into a diphenylmethane derivative and this subsequently being converted by phosgenation into an aromatic isocyanate.

When the colorless amine is, for example, aniline, the aniline can be converted into methylenedianiline (MDA) in at least one further step.

The methylenedianiline (MDA) can then be reacted further to form methylenedi(phenyl isocyanate) (MDI).

The synthesis of MDI is typically carried out in a two-stage process, with aniline firstly being reacted with formaldehyde to form MDA and the MDA subsequently being reacted with phosgene in a second step. The phosgenation of MDA is known to those skilled in the art and is described, for example in H. Ullrich "Chemistry and Technology of Isocyanates", John Wiley, 1996, or WO 2010/057909.

In one embodiment of the invention, the mixture (G2) comprises at least 90% by weight, preferably at least 94% by weight, more preferably at least 96% by weight, particularly preferably at least 99% by weight, of aniline, with the aniline being converted in at least one further step into methylenedianiline (MDA) which is preferably subsequently converted into methylenedi(phenyl isocyanate) (MDI).

In a further preferred embodiment of the present invention, the mixture (G1) is hydrogenated in the presence of a copper-comprising and/or palladium-comprising catalyst. The mixture (G1) in this case preferably comprises at least 90% by weight, more preferably at least 94% by weight, even more preferably at least 96% by weight, particularly preferably at least 99% by weight, of aniline (based on the total weight of the mixture (G1)).

The mixture (G2) after the hydrogenation preferably comprises at least 90% by weight of aniline. Preference is here given to <2% by weight, even more preferably <1% by weight, particularly preferably <0.5% by weight, less aniline being present in the mixture (G2) compared to the mixture (G1) before the hydrogenation. Furthermore, preference is given in this embodiment to the aniline comprised in the mixture (G2) being optionally purified and firstly being converted into MDA using formaldehyde, whereupon MDA is subsequently converted into MDI.

EXAMPLES

The following examples illustrate, by way of example, how the process of the invention can be carried out. The process of the invention is, however, not restricted to the reactions indicated in the examples.

Examples 1-7: Variation of the Catalyst

General Experimental Procedure

Aniline (150 g) is introduced into a 300 ml autoclave. Catalyst (1.5 g) is added thereto. The autoclave is flushed a number of times with nitrogen and the nitrogen is then replaced by pure hydrogen. After heating to 100° C., the hydrogen pressure is set to 40 bar and the mixture is stirred at this pressure and temperature for 12 hours. The autoclave is subsequently cooled and vented and the aniline is taken off, and the color number thereof is then determined.

TABLE 1

| Example | Catalyst | Color number of aniline before hydrogenation L*:a*:b* | Content of aniline before hydrogenation [GC-% by area] | Color number after hydrogenation L*:a*:b* | Content of aniline after hydrogenation [GC-% by area] |
|---|---|---|---|---|---|
| 1 | 60% CuO, 40% Cr$_2$O$_3$ | 67.3:23.3:66.2 | 96.6 | 90.3:1.9:11.5 | 96.1 |
| 2 | 65% CuO, 5% La, 30% Al$_2$O$_3$ | 67.3:23.3:66.2 | 96.6 | 91.9:−1.5:8.2 | 96.5 |
| 3 | 50% CuO 50% Al$_2$O$_3$ | 67.3:23.3:66.2 | 96.6 | 96.6:−0.5:7.8 | 96.6 |

TABLE 1-continued

| Example | Catalyst | Color number of aniline before hydrogenation L*:a*:b* | Content of aniline before hydrogenation [GC-% by area] | Color number after hydrogenation L*:a*:b* | Content of aniline after hydrogenation [GC-% by area] |
|---|---|---|---|---|---|
| 4 | 5% Pd 95% C | 67.3:23.3:66.2 | 96.6 | 98.5:−0.8:5.2 | 94.2 |
| 5 | 65% Co, 25% Cu, 10% Mn | 67.3:23.3:66.2 | 96.6 | 98.2:−3.1:12.4 | 96.0 |
| 6 | Raney Ni | 67.3:23.3:66.2 | 97 | 80:10:30 | 51 |
| 7 | 5% Ru 95% ZrO$_2$ | 67.3:23.3:66.2 | 97 | 82:−0.5:15 | 84 |

Table 1 shows that the use of Cu-comprising catalysts is particularly advantageous since the color number can be significantly improved and the content of aniline remains virtually unchanged. The use of Ni- or Ru-comprising catalysts, on the other hand, does lead to a loss of aniline, but the color number is improved. Both in table 1 above and also in the following text, the sum of the weight of catalyst is always 100% (calculated as % by weight). If the individual amounts indicated add up to less than 100%, the missing percentages are the support material.

Example 8: Variation of the Reaction Time

General Experimental Procedure

Aniline (150 g) is introduced into a 300 ml autoclave. A 50% CuO-50% Al$_2$O$_3$ catalyst (1.5 g) is added thereto. The autoclave is flushed a number of times with nitrogen and the nitrogen is then replaced by pure hydrogen. After heating to 100° C., the hydrogen pressure is set to 40 bar and the mixture is stirred at this pressure and temperature for the indicated time. The autoclave is subsequently cooled and depressurized and the aniline is taken out, and the color number thereof is then determined.

TABLE 2

| Example | Reaction time [h] | Color number of recycled aniline before hydrogenation L*:a*:b* | Content of aniline before hydrogenation [GC-% by area] | Color number after hydrogenation L*:a*:b* | Content of aniline after hydrogenation [GC-% by area] |
|---|---|---|---|---|---|
| 2 | 12 h | 67.3:23.3:66.2 | 96.6 | 91.9:−1.5:8.2 | 96.5 |
| 8 | 48 h | 67.3:23.3:66.2 | 96.6 | 96.8:0.0:8.1 | 96.4 |

The experiments in table 2 show that the reaction time has a great influence on the resulting color number L*, with the latter becoming greater with increasing reaction time and the aniline content remaining the same. However, the proportion of aniline decreases with increasing reaction time.

Examples 9-12: Variation of the Reaction Temperature

General Experimental Procedure

Aniline (150 g) is introduced into a 300 ml autoclave. A 50% CuO-50% Al$_2$O$_3$ catalyst (1.5 g) is added thereto. The autoclave is flushed a number of times with nitrogen and the nitrogen is then replaced by pure hydrogen. After heating to the temperature indicated, the hydrogen pressure is set to 40 bar and the mixture is stirred at this pressure and temperature for 12 hours. The autoclave is subsequently cooled and vented and the aniline is taken out, and the color number thereof is then determined.

TABLE 3

| Example | Reaction temperature [° C.] | Color number of aniline before hydrogenation L*:a*:b* | Content of aniline before hydrogenation [GC-% by area] | Color number after hydrogenation L*:a*:b* | Content of aniline after hydrogenation [GC-% by area] |
|---|---|---|---|---|---|
| 2 | 100 | 67.3:23.3:66.2 | 96.6 | 91.9:−1.5:8.2 | 96.5 |
| 9 | 130 | 67.3:23.3:66.2 | 96.6 | 98.2:0.1:4.9 | 96.6 |
| 10 | 150 | 67.3:23.3:66.2 | 96.6 | 98.4:−0.3:4.9 | 97.1 |

TABLE 3-continued

| Example | Reaction temperature [° C.] | Color number of aniline before hydrogenation L*:a*:b* | Content of aniline before hydrogenation [GC-% by area] | Color number after hydrogenation L*:a*:b* | Content of aniline after hydrogenation [GC-% by area] |
|---|---|---|---|---|---|
| 11 | 180 | 67.3:23.3:66.2 | 96.6 | 99.5:−0.5:3.0 | 96.7 |
| 12 | 200 | 67.3:23.3:66.2 | 96.6 | 99.2:−0.4:2.5 | 96.7 |

The results in table 3 show that the color number can be improved by increasing the reaction temperature. In addition, the content of aniline is greatest at 150° C. (example 10).

Example 13: Distillation to Improve the Color Number

The color number of the hydrogenated samples can be increased further by distillation. For this purpose, aniline from example 10 is distilled by means of a short path distillation at 35 mbar and at a temperature at the bottom of 72° C. The main fraction has a color number of L*=100.0, a*=−0.1, b*=0.3.

Example 14: Continuous Hydrogenation 34 g of catalyst (65% CuO, 5% La, 30% $Al_2O_3$) are introduced into a tube reactor and the latter is made inert by means of nitrogen. The catalyst is subsequently activated by passing hydrogen over it. The aniline is conveyed through the reactor at varying temperature and a hydrogen pressure of 20 bar and with a varying space velocity over the catalyst. The color number and the composition of the output are determined at regular intervals. Some operating points of this experiment are reported in table 4.

TABLE 4

| Time on stream | Temperature [° C.] | Space velocity over the catalyst [kg of feed/l of cat * h] | Proportion of aniline in the mixture [GC-% by area] | L* | a* | b* |
|---|---|---|---|---|---|---|
| Feed | — | — | 95.4 | 92.9 | −5.5 | 40.7 |
| 238 | 100 | 0.30 | 95.5 | 94.1 | −0.1 | 15.5 |
| 309 | 100 | 1.00 | 95.3 | 95.3 | 0.1 | 10.8 |
| 380 | 150 | 0.30 | 95.4 | 98.1 | −0.7 | 5.6 |
| 479 | 125 | 0.30 | 95.4 | 97.1 | −0.4 | 7.9 |
| 551 | 125 | 1.00 | 95.4 | 95.2 | −0.2 | 11.5 |
| 575 | 150 | 1.00 | 95.4 | 96.9 | −0.7 | 9.0 |
| 671 | 170 | 0.65 | 95.1 | 95.3 | −1.1 | 10.8 |
| 695 | 185 | 0.65 | 94.5 | 97.3 | −1.1 | 8.7 |
| 719 | 200 | 0.65 | 94.1 | 97.9 | −0.9 | 6.8 |
| 815 | 200 | 1.00 | 94.9 | 97.1 | −0.5 | 8.5 |
| 860 | 150 | 0.65 | 95.3 | 97.0 | 0.2 | 6.8 |
| 884 | 150 | 0.65 | 95.3 | 96.8 | 0.1 | 7.7 |
| 912 | 150 | 0.65 | 95.4 | 97.4 | 0.2 | 6.0 |
| 1028 | 150 | 0.65 | 95.3 | 96.9 | 0.1 | 7.6 |
| 1148 | 150 | 0.65 | 95.4 | 95.9 | 0.0 | 9.7 |
| 1202 | 150 | 0.65 | 95.4 | 95.7 | −0.1 | 11.5 |

The experiments reported in table 4 show that the catalyst used is stable in the long term.

Ex. 15: Continuous Hydrogenation 21 g of catalyst (50% CuO, 50% $Al_2O_3$) are introduced into a tube reactor and the latter is made inert by means of nitrogen. The catalyst is subsequently activated by passing hydrogen over it. The recycled aniline is conveyed through the reactor at varying temperature and a hydrogen pressure of 20 bar and with a varying space velocity over the catalyst. The color number and the composition of the output are determined at regular intervals. Some operating points of this experiment are reported in table 5.

TABLE 5

| Time on stream | Temperature [° C.] | Space velocity over the catalyst [kg of feed/l of cat * h] | Proportion of aniline in the mixture [GC-% by area] | L* | a* | b* |
|---|---|---|---|---|---|---|
| Feed | — | — | 95.5 | 86.6 | −1.2 | 59.6 |
| 113 | 150 | 0.65 | 95.2 | 88.6 | 1.6 | 29.0 |
| 139 | 170 | 0.65 | 95.1 | 89.9 | 0.6 | 25.8 |
| 161 | 190 | 0.65 | 94.7 | 91.6 | −0.1 | 22.8 |
| 281 | 190 | 0.65 | 95.0 | 84.4 | 2.5 | 25.0 |
| 305 | 200 | 0.65 | 94.8 | 93.5 | −1.3 | 19.7 |
| 401 | 210 | 0.65 | 94.8 | 94.9 | −0.3 | 14.3 |
| 427 | 220 | 0.65 | 94.9 | 94.30 | −0.4 | 16.6 |

At the same space velocity over the catalyst, the L* value becomes greater with increasing temperature, but the proportion of aniline decreases.

Example 16: Synthesis of MDI Using Color-Improved Aniline

Aniline is converted into MDI according to the following method.

The synthesis of MDA is carried out in a 2l double-wall reactor equipped with a propeller stirrer. The aniline from example 13 is admixed with aqueous hydrochloric acid (32% by weight) and heated to 90° C. A 36.5% strength by weight aqueous formaldehyde solution is then added, with the reaction temperature being maintained at 90° C. After all the formaldehyde had been added, the reaction mixture is heated to 120° C. for 2 hours and then neutralized using 50% strength by weight aqueous NaOH solution and subsequently washed twice with water.

The MDA obtained in this way is added to 1300 ml of monochlorobenzene and added dropwise to a solution of monochlorobenzene and phosgene (100 g) at 50° C. over a period of 60 minutes. The reaction mixture is subsequently heated at 100° C. for 30 minutes until it is clear. The excess phosgene is removed by application of a reduced pressure of 20 mbar at 75° C. The MDI obtained is dechlorinated firstly for 60 minutes at 100° C. and 50 mbar, then for 60 minutes at 180° C. and 20 mbar. After cooling to room temperature, the color number and also the NCO number and the chlorine content are determined.

TABLE 6

| Example | Aniline | Color number of the MDI L*:a*:b* | NCO number of the MDI |
|---|---|---|---|
| 11 | Aniline | 84.3:−3.2:54.9 | 32.4 |
| 13 | Aniline from example 11 | 95.0:−7.2:33.2 | 32.7 |

The examples in table 6 show that the color of the MDI can be significantly improved by the use of hydrogenated aniline. The NCO number, an important quality criterion for MDI, remains virtually unchanged.

The invention claimed is:

1. A process for hydrogenating a mixture (G) which comprises at least one colorless amine and at least one color-imparting component, the process comprising:
hydrogenating the mixture (G) in the presence of a catalyst to obtain a mixture (G2) in which the at least one color-imparting component is at least partially or completely hydrogenated, and
converting the at least one colorless amine comprised in the mixture (G2) into a diphenylmethane derivative, and optionally converting the diphenylmethane derivative into an aromatic isocyanate, optionally by phosgenation;
wherein the at least one color-imparting component is selected from the group consisting of a cycloaliphatic carbonyl compound, a cycloaliphatic amine, a cycloaliphatic imine and a C6-ring aromatic.

2. The process of claim 1, wherein the at least one colorless amine is a primary amine, an aromatic amine and/or a monoamine.

3. The process of claim 1, wherein the mixture (G2) has a color number L* of at least 90 as measured in accordance with DIN 5033 (2009), a color number b* of not more than 20 as measured in accordance with DIN 5033 (2009), or both.

4. The process of claim 1, wherein at least 90% by weight of the at least one colorless amine, based on a total amount of the at least one colorless amine comprised in the mixture (G1), is present in the mixture (G2) after the hydrogenating.

5. The process of claim 1, wherein the at least one colorless amine is present in the mixture (G1) in an amount of at least 80% by weight, based on a total weight of the mixture (G1).

6. The process of claim 1, wherein the at least one color-imparting component is present in the mixture (G1) in an amount of not more than 5% by weight, based on a total weight of the mixture (G1).

7. The process of claim 1, wherein the catalyst comprises copper, palladium, cobalt, rhenium, manganese, or a mixture of at least two thereof.

8. The process of claim 7, wherein the catalyst comprises at least one of:
i) copper in an amount in a range of from 0.1 to 100% by weight, based on a total weight of the catalyst and calculated as metal; and
ii) palladium in an amount in a range of from 0.1 to 100% by weight, based on a total weight of the catalyst and calculated as metal.

9. The process of claim 7, wherein at least one of the following is satisfied:
i) if the catalyst comprises copper, then the copper is present as a metal, a copper compound, a mixture of at least two copper compounds, a mixture of a metal and a copper compound or a mixture of a metal and at least two copper compounds, optionally wherein the copper compounds are selected from the group consisting of copper chromate, copper chromite, copper oxide, copper nitrate, copper sulfate, copper chloride, copper bromide, copper iodide, copper carbonate, copper acetylacetate, copper alkoxide, copper aryloxide and copper carboxylate; and
ii) if the catalyst comprises palladium, then the palladium is present as a metal, a palladium compound, a mixture of at least two palladium compounds, a mixture of a metal and a palladium compound or a mixture of a metal and at least two palladium compounds.

10. The process of claim 1, wherein the at least one color-imparting component is selected from the group consisting of a cyclohexylphenylamine derivative, a cyclohexanone derivative, a cyclohexenone derivative, a cyclohexylamine derivative, an N-methylcyclohexylamine derivative, a toluidine derivative, a nitrobenzene derivative, a 2-aminophenol derivative, a 1,2-phenylenediamine derivative, a diphenylamine derivative, an oxidized N-methylaniline derivative and an unoxidized N-methylaniline derivative.

11. The process of claim 1, wherein at least one of the following conditions is satisfied:
i) a temperature during the hydrogenating is in a range of from 90° C. to 300° C.;
ii) a duration of the hydrogenating is in a range of from 1 to 100 hours;
iii) the hydrogenating is carried out using hydrogen gas ($H_2$); and
iv) the process is carried out continuously or batchwise.

12. The process of claim 1, wherein at least one of the following conditions is satisfied:
i) the catalyst is present in supported or unsupported form, wherein if the catalyst is present in supported form, then the support material is optionally selected from the group consisting of carbon, silicon oxide, aluminum oxide, manganese oxide, cerium oxide, zirconium oxide, lanthanum oxide, titanium oxide and mixtures thereof; and
ii) the catalyst is in the form of powder or shaped bodies.

13. The process of claim 1, further comprising:
working up the mixture (G2) to isolate the at least one colorless amine, to separate off the catalyst and/or to remove the hydrogenation products from the mixture (G2), optionally wherein the working up comprises distillation.

14. The process of claim 1, wherein:
the mixture (G2) comprises at least 90% by weight of aniline; and
the process further comprises converting the aniline into methylenedianiline (MDA).

15. The process of claim 14, further comprising:
converting the methylenedianiline (MDA) into methylenedi(phenyl isocyanate) (MDI).

16. The process of claim 1, wherein the mixture (G1) is recycled aniline, where the recycled aniline comprises at least one color-imparting component selected from the group consisting of a cycloaliphatic carbonyl compound, a cycloaliphatic amine, a cycloaliphatic imine and a C6-ring aromatic.

* * * * *